United States Patent
Raphael et al.

(10) Patent No.: US 11,702,622 B2
(45) Date of Patent: Jul. 18, 2023

(54) VITRO CHARACTERIZATION OF CELL INJURY DUE TO MECHANICAL BLUNT

(71) Applicant: The Government of the United States of America, as represented by the Secretary of the Navy, Arlington, VA (US)

(72) Inventors: Marc P. Raphael, Springfield, VA (US); Wonmo Kang, Springfield, VA (US)

(73) Assignee: The Government of the United States of America, as represented by the Secretary of the Navy, Washington, DC (US)

(*) Notice: Subject to any disclaimer, the term of this patent is extended or adjusted under 35 U.S.C. 154(b) by 424 days.

(21) Appl. No.: 16/999,174

(22) Filed: Aug. 21, 2020

(65) Prior Publication Data
US 2021/0054325 A1 Feb. 25, 2021

Related U.S. Application Data

(60) Provisional application No. 62/890,108, filed on Aug. 22, 2019.

(51) Int. Cl.
| C12M 1/12 | (2006.01) |
| C12M 3/00 | (2006.01) |
| C12N 5/071 | (2010.01) |
| C12M 1/00 | (2006.01) |
| C12M 1/42 | (2006.01) |
| C12M 1/32 | (2006.01) |

(52) U.S. Cl.
CPC ............ *C12M 25/04* (2013.01); *C12M 21/08* (2013.01); *C12M 23/12* (2013.01); *C12M 23/34* (2013.01); *C12M 35/08* (2013.01); *C12N 5/0602* (2013.01)

(58) Field of Classification Search
CPC ...... C12M 25/04; C12M 21/08; C12M 23/12; C12M 23/34; C12M 35/08; C12M 35/04; C12M 41/46; C12M 41/48; C12M 41/36; C12N 5/0602
See application file for complete search history.

(56) References Cited

U.S. PATENT DOCUMENTS

2002/0106625 A1* 8/2002 Hung ............... C12M 25/14
435/395
2007/0026517 A1* 2/2007 Schulz ............. C12M 21/08
435/325

* cited by examiner

*Primary Examiner* — Michael L Hobbs
(74) *Attorney, Agent, or Firm* — US Naval Research Laboratory; Rebecca Forman

(57) ABSTRACT

A system and method for studying cell injury mechanisms by applying biologically relevant mechanical impact to in vitro cell culture are disclosed. This approach is for maintaining consistent in vitro conditions during experiments, accommodating multiple cell populations, and monitoring each in real-time while achieving amplitude and time scale of input acceleration that mimic blunt injury cases. These multiplexed, environmental control capabilities enable characterizing the relationships between mechanical impact and cell injury in multivariate biological systems.

6 Claims, 11 Drawing Sheets

VITRO CHARACTERIZATION OF CELL INJURY DUE TO MECHANICAL BLUNT

This application claims the benefit of U.S. Provisional Application No. 62/890,108, filed on Aug. 22, 2019 by Marc P. Raphael et al., entitled AN EXPERIMENTAL APPARATUS FOR IN VITRO CHARACTERIZATION OF CELL INJURY DUE TO MECHANICAL BLUNT, the disclosure of which is incorporated herein by reference in its entirety.

BACKGROUND

Aspects of the exemplary embodiment relate to the response of cells when subjected to mechanical impact and find particular application in connection with the characterization of cell injury using live cell microscopy.

Trauma is one of the leading causes of death in the world and has garnered much interest in recent years due to the realization of the breadth of impact-related pathologies that vary in severity, level of ability for accurate diagnosis, and time scales over which the effects are observed. For instance, blunt liver trauma is often associated with a single severe traumatic incident and might involve immediate surgical intervention once identified. However, traumatic brain injuries (TBI) often have a singular traumatic event, yet can manifest as a combination of physical, cognitive or emotional defects over time that can be misdiagnosed as post-traumatic stress syndrome. Furthermore, the recently discovered prevalence of chronic traumatic encephalopathy (CTE) in contact sports athletes is associated with compounding effects of less-severe, yet still traumatic events over time that can only be accurately diagnosed posthumously.

Many resources and efforts have been utilized over the years to better understand the pathophysiology of blunt impact injuries. Typically, animal models that utilize injury mechanisms to the organ of interest in conjunction with end-point assays, such as immunohistochemistry, have been a common platform to identify injury related biomarkers or to assess cell/tissue damage. However, the mechanisms underlying post-trauma cellular damage or death remain poorly understood, likely in part due to the lack of standard testing procedures and the complexity of interpreting animal models. This has prompted research efforts to focus on simpler in-vitro platforms, allowing researchers to investigate potential underlying injury mechanisms at the cellular or molecular level. However, in many of these in-vitro platforms, it has proven technically challenging to accurately apply injury-relevant pressure forces to the cell population in question in tightly controlled environments.

The human body is exposed to considerably large linear acceleration in the range of 80-250 G during mechanical collisions, e.g., football and boxing matches or military operations. Such rapid acceleration of the human body results in various traumatic injuries including blunt liver trauma or traumatic brain injury. It is important to note that acceleration alone is the most commonly used criteria for assessment of blunt injury. However, acceleration-induced pressure gradients in the abdomen or skull is expected to be the dominant damage mechanism and, as a result, understanding the dynamic response of biological systems due to time-dependent local pressure associated with rapid acceleration during impact is a crucial step towards accurate prediction of blunt injury and implementing novel therapeutic strategies post-trauma.

As an example, dynamic cavitation in the brain is increasingly considered a potential damage mechanism for traumatic brain injury. In this regard, one notable advance is in the characterization of cavitation properties for soft biomaterials under an impulsive force. In these studies, the critical acceleration that corresponds to the onset of the bubble formation and bursts has been experimentally and theoretically characterized utilizing biologically relevant soft biomaterials including collagen, agarose, and gelatin. These studies have established a range of mechanical acceleration for potential cavitation-induced brain injury. Further, these studies have shown that the acceleration-induced local pressure strongly depends on the sample size, and therefore, in addition to acceleration, the size of biological system experiencing trauma, e.g., head, should be considered for accurate assessment of potential injuries.

Despite the recent progress on the dynamic response of tissue simulant, experimental studies on the spatio-temporal response of live cells under well-characterized acceleration-induced pressure are very limited in the literature largely due to lack of such experimental capability. Some of key experimental challenges include: maintenance of consistent in vitro conditions during the experiments and observation periods; a capability to probe cells in time, in particular before and after impact; and a high throughput approach for analyses of multiplexed cell populations. The combination of these capabilities are necessary for revealing cellular behavior associated with injury mechanisms and ensuring statistical significance considering the heterogeneous nature of cell response. For example, understanding and characterizing the cell-line specific senescence for in-vitro platforms is important to accurately probe underlying mechanisms and ensure reproducible results.

Additionally, while the causes of blunt injuries are highly dynamic, conventional wound healing assays are based upon mechanical loading of cells with unquantified forces and unrealistically slow time scales. The most common wound healing assay incorporates a single layer of cells grown on a culture dish. Then the cells are locally removed by using various means including a plastic tip, stamps, electrical current, and focused laser to simulate the wound. The rate at which the cells fill the scratch is used as a metric for how efficiently a particular cell type can contribute to the wound healing process. These approaches fail to effectively mimic the dynamic natures of blunt injuries.

Electrical pulses or focused laser are often used to mimic dynamically induced cavitation bubbles during blunt and resultant neuronal damage. However, possible thermal effects due to localized heating of cell media is a major confounding factor. Also capabilities for multiplexing and long-term observations (weeks) are not available.

Thus, it would be desirable to investigate damage mechanisms of live cells to address the key injury mechanisms, e.g., acceleration and/or pressure, and injury criteria associated with mechanical impact.

BRIEF DESCRIPTION

Mechanical impact and the resulting acceleration-induced pressure gradient on the human body is one of the main mechanisms for traumatic injury. Fundamental understanding of injury mechanisms associated with mechanical impact is essential toward the development of reliable injury criteria and more accurate prediction of injury. In addition, such knowledge would pave innovative ways to better protective equipment and effective strategies for post-injury treatment.

In accordance with one aspect of the exemplary embodiment, a system and method for in vitro characterization of cell injury due to mechanical blunt includes applying a well-controlled mechanical impact to live cells cultured in an in vitro setup compatible with live cell microscopy. This embodiment is capable of applying well-characterized and reproducible acceleration-induced pressure gradients that is compatible with long-term and environmentally controlled live-cell microscopy. The in vitro platform allows close monitoring of multiple cell populations, down to individual cells, to deduce how impact affects cell viability and mitosis, as well as investigate potential molecular mechanisms of cell injury, such as membrane permeabilization due to pressure gradients. The invention allows 1) maintenance of consistent in vitro conditions during the experiments and observation periods; 2) a capability to probe cells in time, in particular before and after impact; 3) high throughput analyses of multiplexed cell populations; and 4) application of mechanical impact that is relevant to the common blunt injuries. These capabilities allow for characterizing dynamic cell response associated with injury mechanisms.

In accordance with another aspect of the exemplary embodiment, continuous optical observation of multiple cell culture populations (at least up to 12 separate culture populations) can be performed without the need to take cells out from an incubator for observation. Additionally, the multiplexing capability of multiple cell populations in parallel offers a unique dynamic window into how cells respond to mechanical input by directly comparing the same population of cells before and after impact in real time. These attractive capabilities allow for proving the injury mechanisms of cells while minimizing batch-to-batch and/or population-to-population variations in cell response due to heterogeneity.

Advantages of the present invention include its capability of applying well-characterized and reproducible acceleration-induced pressure gradients that is compatible with long-term and environmentally controlled live-cell microscopy. The in vitro platform allows close monitoring of multiple cell populations, down in individual cells, to deduce how impact effects cell viability and mitosis, as well as investigate potential molecular mechanisms of cell injury, such as membrane permeabilization due to pressure gradients.

BRIEF DESCRIPTION OF THE DRAWINGS

FIGS. 3G and 3H show live cell images corresponding to C3 in FIG. 3F before (FIG. 3G) and after (FIG. 3H) the impact. FIGS. 3I and 3J show high speed camera images of the cell culture setup during the 40 cm drop. FIG. 3I shows an image before impact. FIG. 3J is an image during impact showing cativation bubbles on the petri dish (indicated by arrows).

DETAILED DESCRIPTION

Methods and systems for in vitro characterization of cell injury due to mechanical blunt are disclosed wherein a well-controlled impact is applied to live cell populations in vitro to mimic blunt injury scenarios using a drop-tower based setup designed to apply a wide range of acceleration while optically monitoring an in vitro cell culture. Pressure in a cell culture chamber during impact is used to establish an acceleration-pressure relation during impact, and damage to cell is evaluated. Acceleration- and cavitation-induced pressure during impact are quantified to characterize the injury mechanism to cells.

In embodiments disclosed herein, a system and method use a multiplexed approach to apply biologically relevant mechanical impact to in vitro cells for characterizing blunt injuries to the cell. The invention can be integrated with other technologies including various live cell imaging instruments, micro/nanodevices, and drop tower systems.

In Vitro Setup for Blunt Injury Mechanisms

Acceleration for typical blunt injuries is in the range of 80 G-250 G within 0.1-10 millisecond. Considering the specific characteristics, it is important to control collisions so that they closely represent biologically relevant blunt injury events during in vitro studies. In this regard, an in vitro setup is integrated with a drop-tower-based system as well as a multiplexed, live cell-imaging instrument, as shown in FIG. 1A.

Figure 1A:
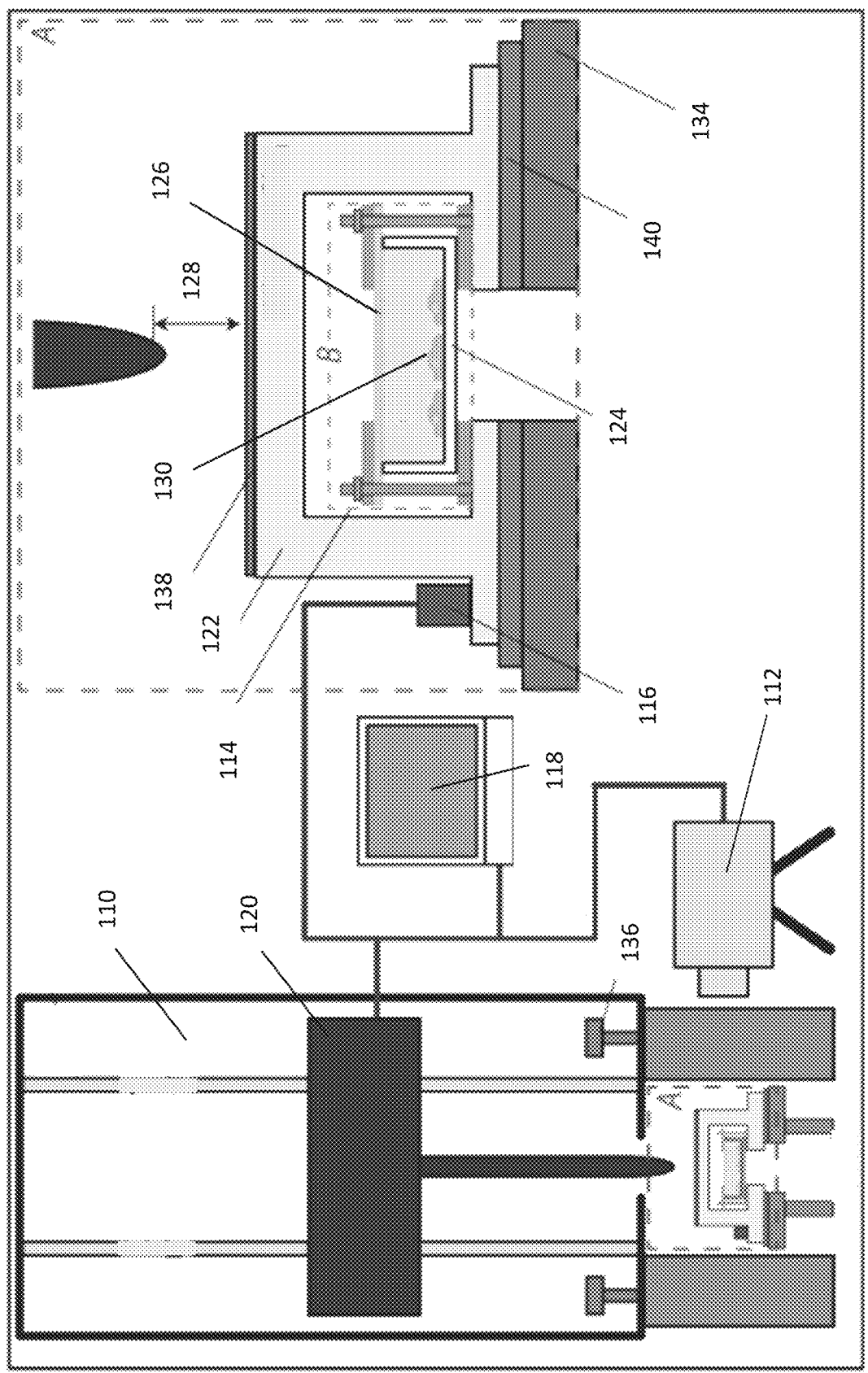
FIG. 1A is a schematic diagram of a drop-tower based integrated system for characterizing biological response of live cells due to rapid acceleration associated with mechanical impact. The inset (zoom in of area A) on the right shows the structures of the cell culture setup and the holder with electrical connections for data acquisition.

As shown in FIG. 1A, one embodiment comprises a conventional drop tower impact system 110, high speed cameras 112, a cell culture setup 114, brakes 136, accelerometers 116, and a data-acquisition system 118. For applying impact on the cell culture setup 114, a weight 120 is vertically lifted to a specific drop height 128 and then released. Upon release, the weight 120 impacts a holder 122 with an integrated cell culture setup 114 causing the cells and cell culture media to rapidly accelerate in the similar way biological systems would accelerate, e.g., inside the abdomen or skull. During impact, velocity, acceleration, and impact force are quantified using various sensors while optically monitoring the cell culture setup 114 utilizing high-speed cameras 112. Before and after an impact experiment, the cell culture petri dish 124 is kept in an incubator (FIG. 1B) for various analyses via live cell microscopy.

The cell culture setup 114 comprises a 35 mm cell culture petri dish 124, cells 130 on the petri dish, aluminum plate, an anvil 134, and a transparent silicone film 126 assembled by standard bolts and nuts for ease of assembly/disassembly. Two technical challenges for any in vitro experimental platform include environmental control and cell heterogeneity. First, cells are sensitive to changes in their environment and, as a result, minimizing and eliminating unwanted perturbations to cellular environments during in vitro studies is important for accurate interpretation and reproducibility of results. Second, both individual and collective cellular behavior is heterogeneous in nature, potentially confounding the interpretation of cellular response associated with the injury mechanism. The cell culture setup 114 is designed to address these challenges by integrating with a multiplexed, live cell imaging instrument shown schematically in FIG. 1B.

The cell holder 122 is designed to be rigid enough to sustain impacts while preventing direct impact to the cell culture setup. Soft foam 1 138 is used at the top of the holder 122 and soft foam 2 140 is used at the bottom of the holder 122 to achieve desired impact in terms of both amplitude and time scale of acceleration. The soft foam 1 138 layer is thinner (1 mm) and stiffer (4 MPa) to prevent direct solid-solid surface impact, which would generate shock waves, while effectively accelerating the holder 122. The soft foam 2 140 layer is thicker (12 mm) and softer (0.4 MPa) so that the holder 122 can vertically move against the small stiffness of the layer. These parameters are specifically chosen to stimulate common blunt injury scenarios, i.e., >150 G and <1 ms. This setup is general to that the system parameters, e.g., the soft foams, can be tuned to mimic characteristics of different blunt injury cases.

Multiplexed In Vitro Cell Cultures

Figure 1B:
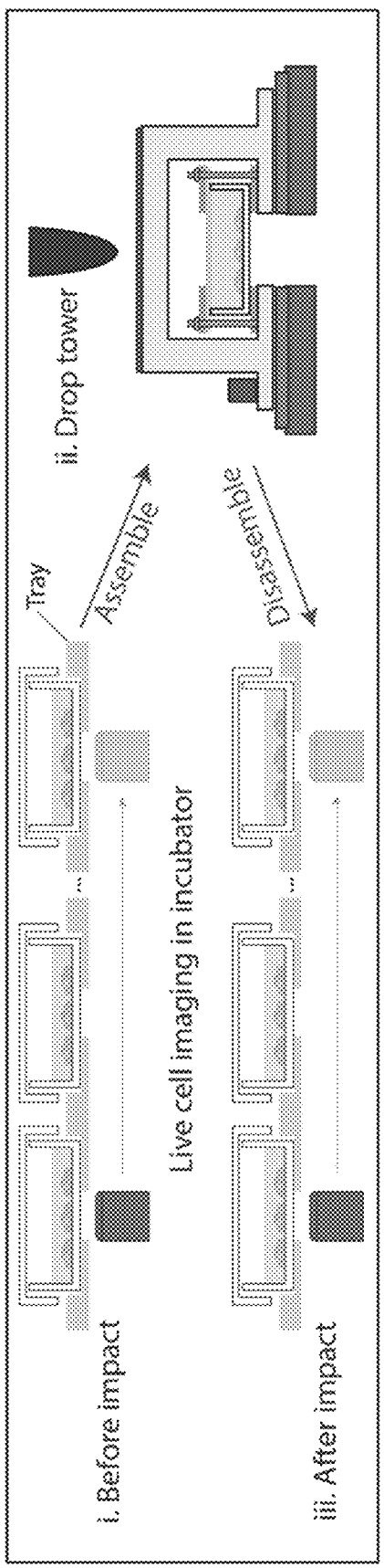
FIG. 1B shows the experimental protocol to study acceleration-induced cell damage utilizing both live cell microscopy and the drop-tower instrument where multiple cell culture petri dishes are prepared and monitored in an incubator. When cell populations reach a specific target stage (e.g., 35-40% confluency in the cell growth curve), each petri dish is assembled with a holder for drop tower experiments. After a drop tower experiment, the petri dish is disassembled for continuing live cell imaging.

For experimental study of cell damage due to mechanical impact, multiple cell culture petri dishes are prepared and monitored using live cell imaging capability in an incubator (FIG. 1B). After the cells cultured on an individual petri dish reach a specific target stage, e.g., 35-40% confluency in the cell growth curve, a petri dish is assembled, after adding additional cell culture media, with a cell culture setup and then with a holder for drop tower experiments (FIG. 1B). Note that two dishes are used for control experiments, while other dishes are for drop tower experiments. To quantify cell population, the local confluency is continuously monitored at each area from A3 to E3 (see FIG. 2) as well as the average confluency of each dish (the average over the nine areas) during cell culture concurrently for both the controls and other dishes. The confluency is the ratio of the area covered by cells to the total area, which is evaluated based on image analysis of cells.

It is important to note that cell culture media is added to the maximum capacity of a petri dish (~10 mm in height) during assembly as shown in FIG. 1B to 1) maintain 3-5 mm deep cell culture media during regular cell culture and 2) remove excessive air from the cell culture setup during drop tower experiments. The shallow cell culture media is important for $CO_2$ exchange that ensures media pH stability. Also, a trapped air pocket between cell culture media and a silicone film during the assembly of the cell culture setup could result in unwanted cell damage during impact. It has been observed that the trapped air was inserted into the cell culture media during violent impact. In this case, cells could be damaged when directly exposed to the air, which is not a biologically relevant mechanism.

Unless stated otherwise, the same volume of cell culture media, like the other dishes, is added to the controls for maintaining consistent in vitro conditions during experiments. After adding media, one (Control 1) is immediately returned to an incubator without being assembled with the cell culture setup while the other one (Control 2) undergoes the exact conditions, like the other dishes, i.e., assembled and stored in a temperature-controlled box for ~10 minutes, except application of impact.

Figure 2:
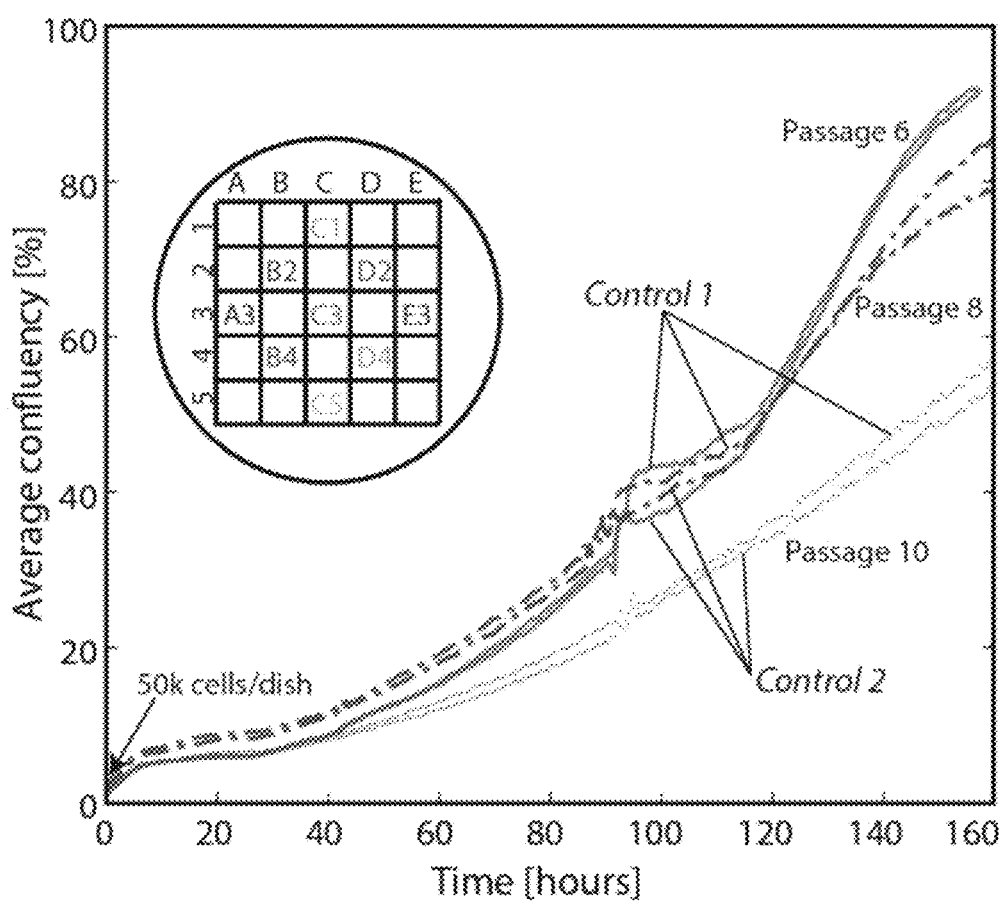
FIG. 2 shows the average confluence over time for two controls that are not exposed to mechanical impact. The average confluency is evaluated for nine areas (A3 to E3).

FIG. 2 shows the average confluency of fibroblast cells for Control 1 and 2 prepared from Passage 6, 8, and 10, respectively. The confluency curves of the two controls are very comparable to each other at all three passages. This study indicates that the in vitro cell culture setup minimizes unwanted perturbations to cell cultures for ~1 week.

Two interesting observations from FIG. 2 are that the growth rate becomes noticeably slower for Passage 10 compared to the previous passages and local confluency curves of each can be significantly different from the average values. The observed, intrinsic temporal and spatial cell heterogeneity could mask or mislead studies on injury mechanisms. As an example, without the multiplexing capability, one may be limited to utilize one cell population at a time, e.g., one cell population from Passage 8 and 10, respectively. If 5 cm and 10 cm drops were applied to cell populations from Passage 8 and 10, respectively, one could conclude that the slower growth rate was due to the mechanical inputs. Similarly, making conclusions based on the data from a localized small area could be misleading because each area even on the same petri dish could have significantly different cell population/behavior/growth compared to the average cell behavior. The examples above highlight the attractive features of the present approach including characterization of the multiple, identical cell culture populations to a variety of impact accelerations and pressure gradients and a capability to analyze a sufficiently large cell population for statistically significant results.

Quantifying the Blunt Injury

To quantify the critical blunt that results in cell damage to fibroblast cells, several cell cultures prepared from Passage 6, 8, and 11 (the same cells used in FIG. 2) were subject to a range of drop tower heights from 5 cm to 40 cm during the middle (35-40%) of their logarithmic growth phase (FIGS. 3A-3J).

Figure 3A:
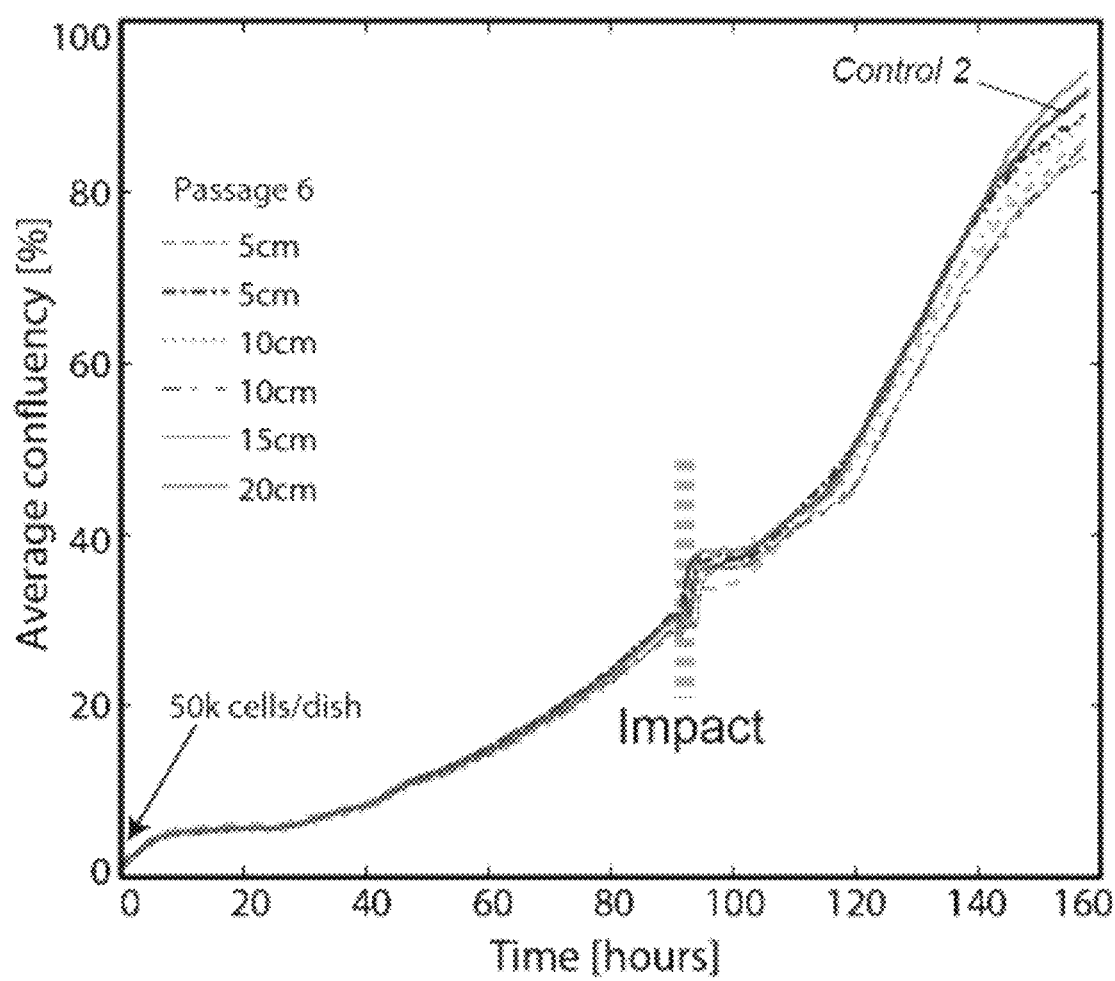
FIGS. 3A-3J show the characterization of the critical mechanical impact for cell injury using Hs27 cells. The average confluency curves provide data for 160 hours of monitoring for a 5 cm single drop, a 10 cm single drop and a 20 cm single drop (FIG. 3A); a 15 cm single drop, a 20 cm single drop, a 10 cm five time drop, a 15 cm five time drop, and a 20 cm five time drop (FIG. 3B); and a 30 cm single drop and a 40 cm single drop on the cell cultures. Passage 6, 8, and 11 were used for the data in FIGS. 3A, 3B, and 3C, respectively. The acceleration measured during the 30 cm and 40 cm drops are shown in the inset of FIG. 3C. The local confluency curves for Control 2, the 30 cm drop, and the 40 cm drop from FIG. 3C are shown in FIGS. 3D, 3E, and 3F, respectively.
Figure 3B:
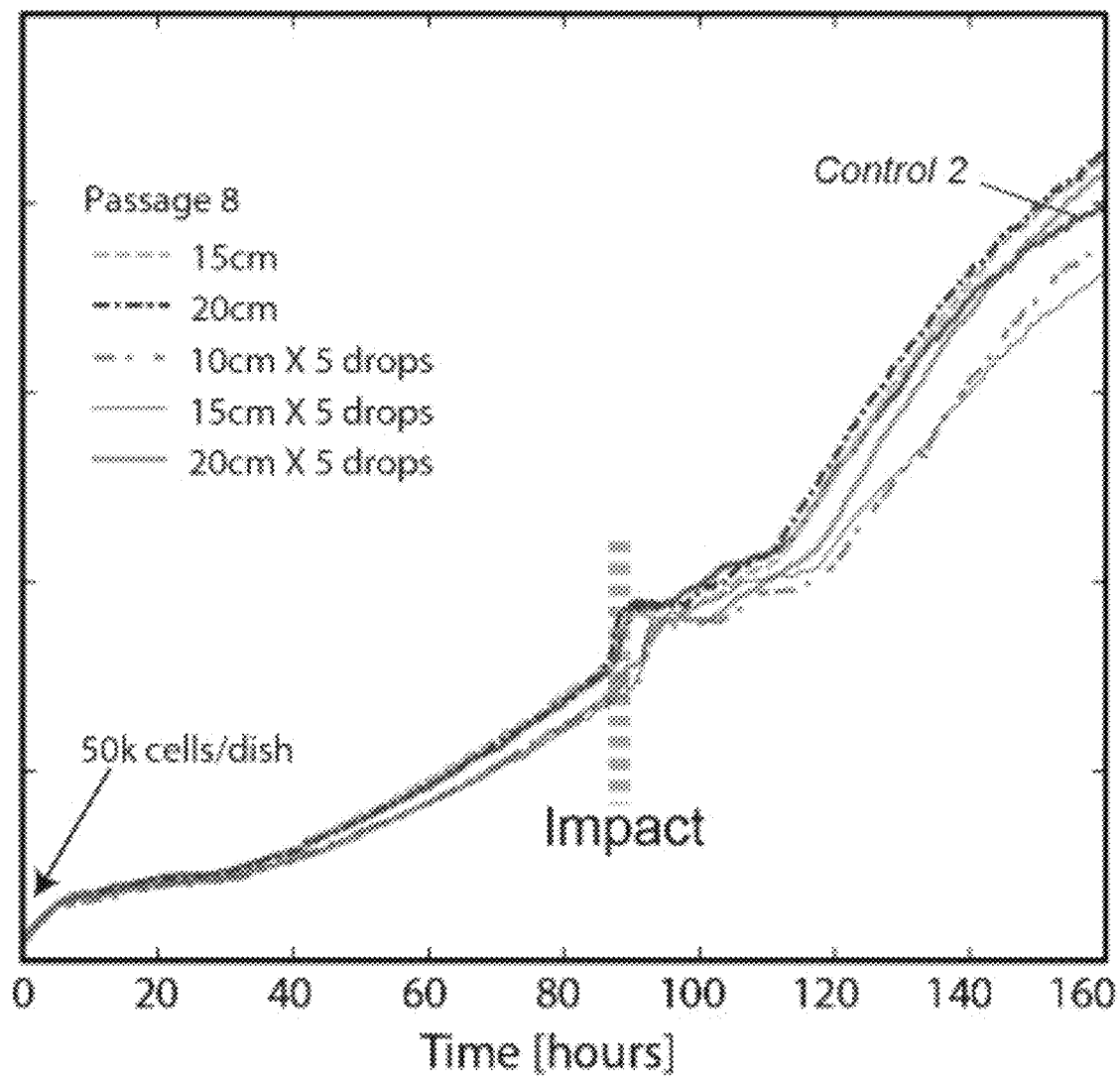
Figure 3C:
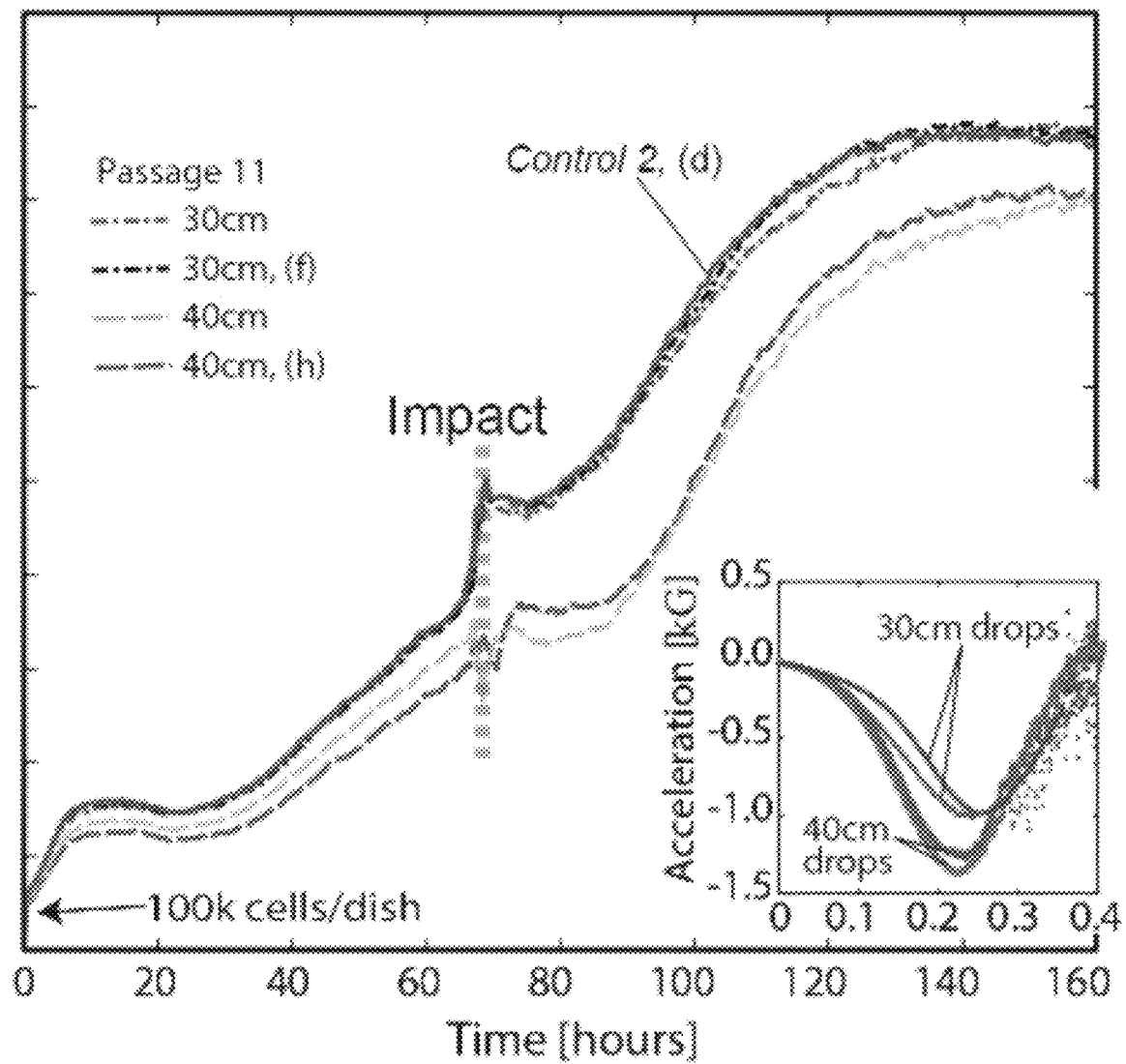
Figure 3D:
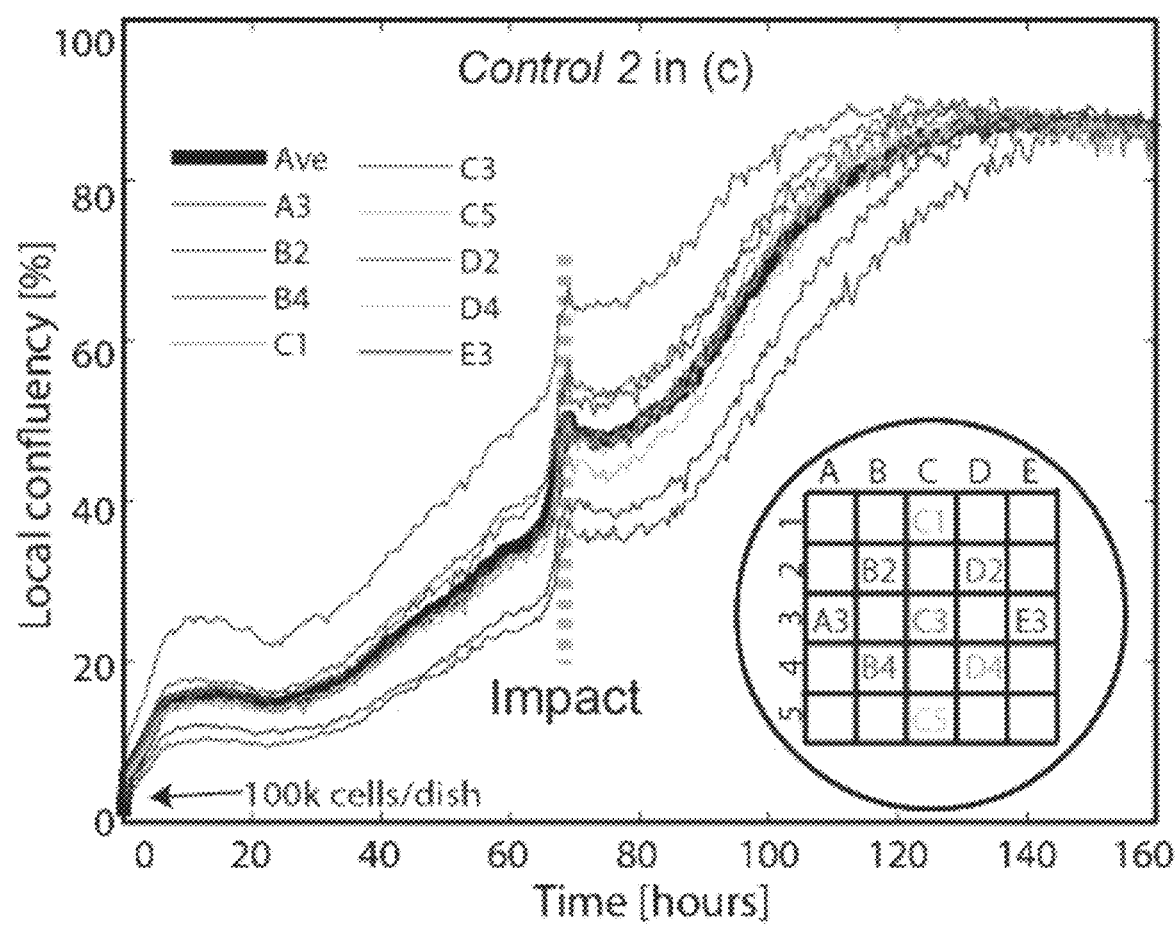
Figure 3E:
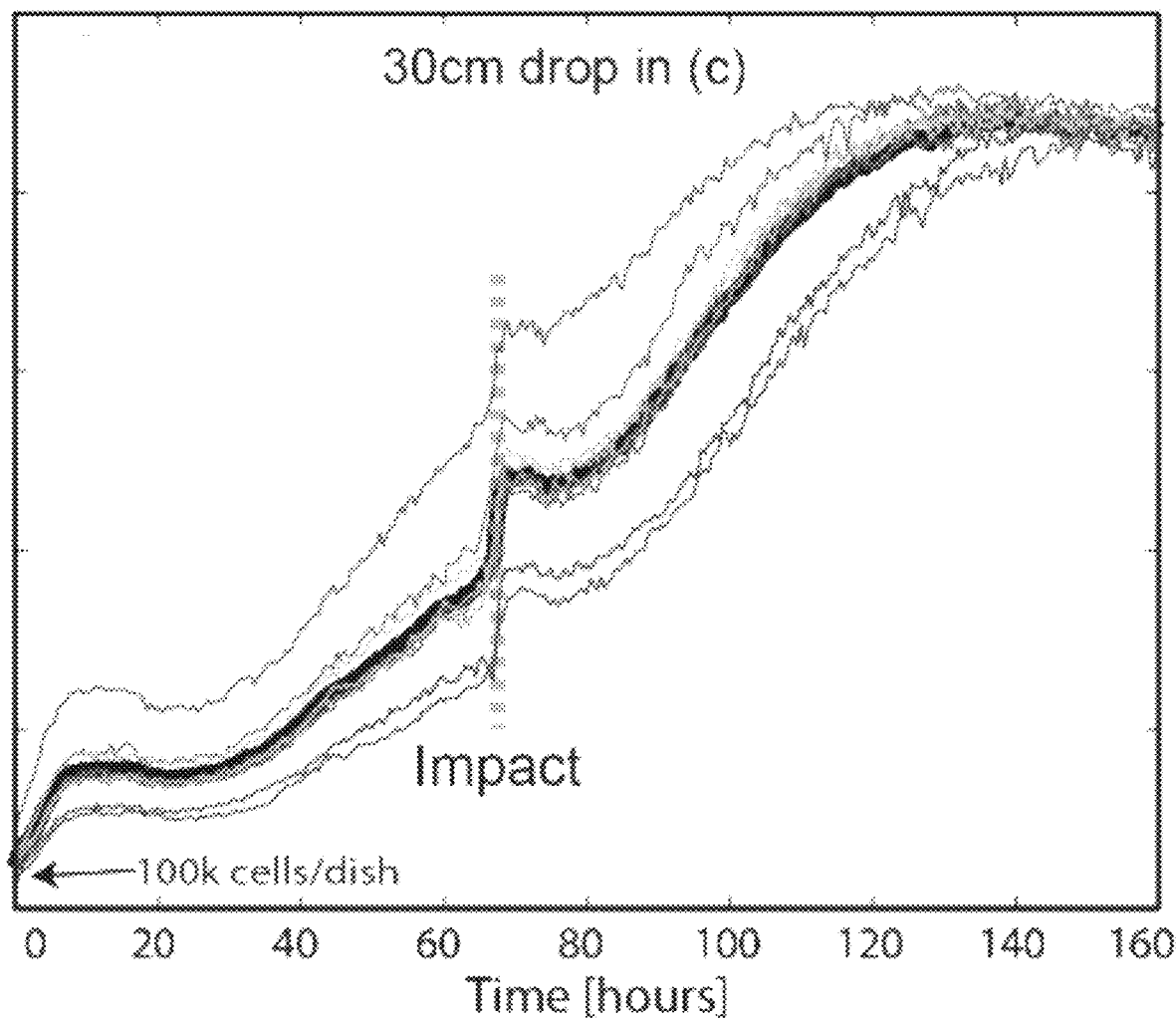
Figure 3F:
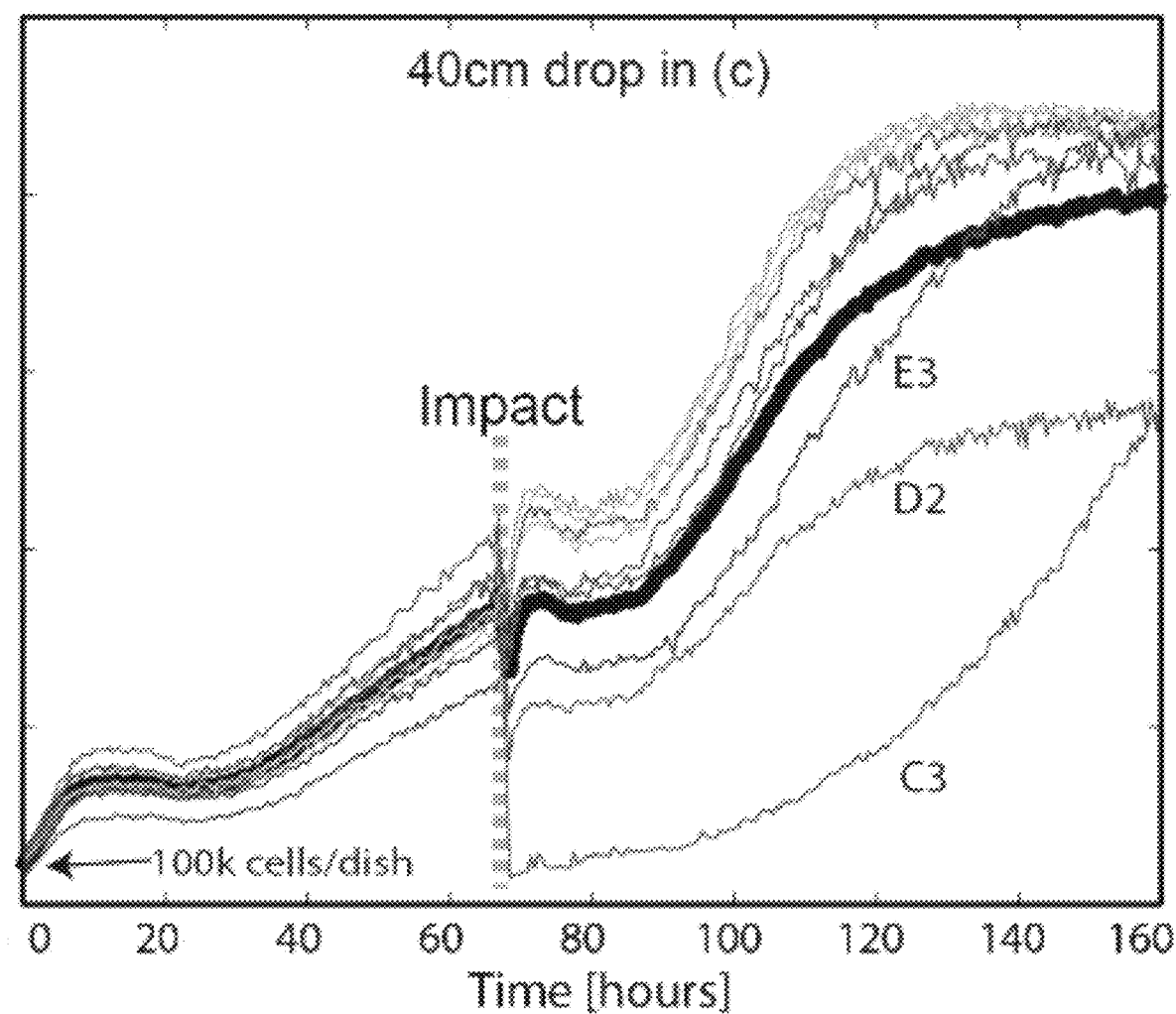
Figure 3G:
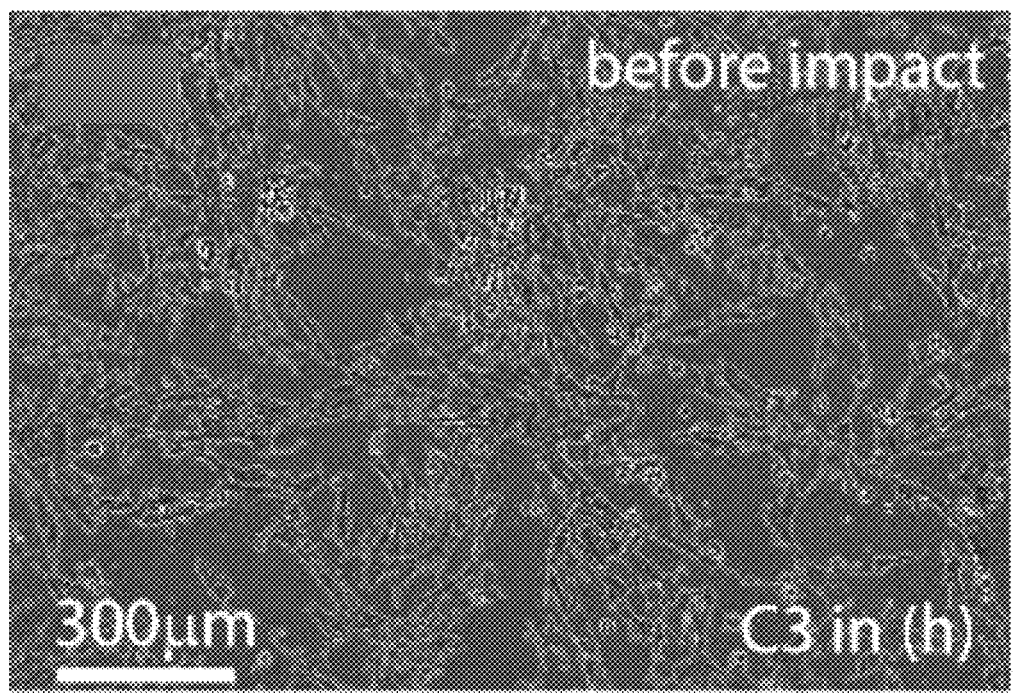
Figure 3H:
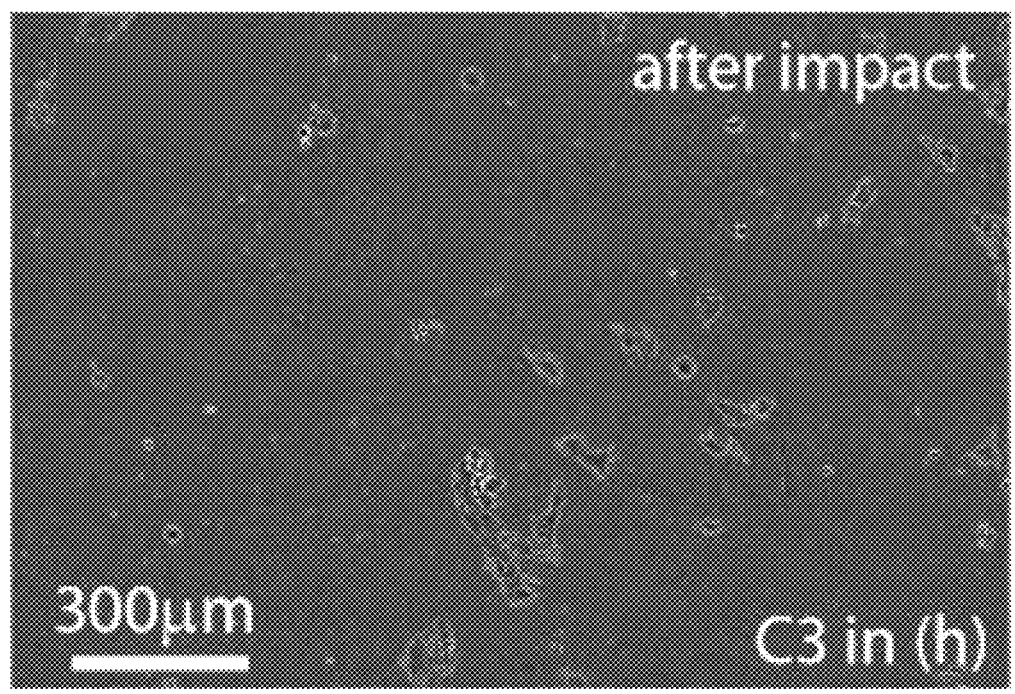
Figure 3I:
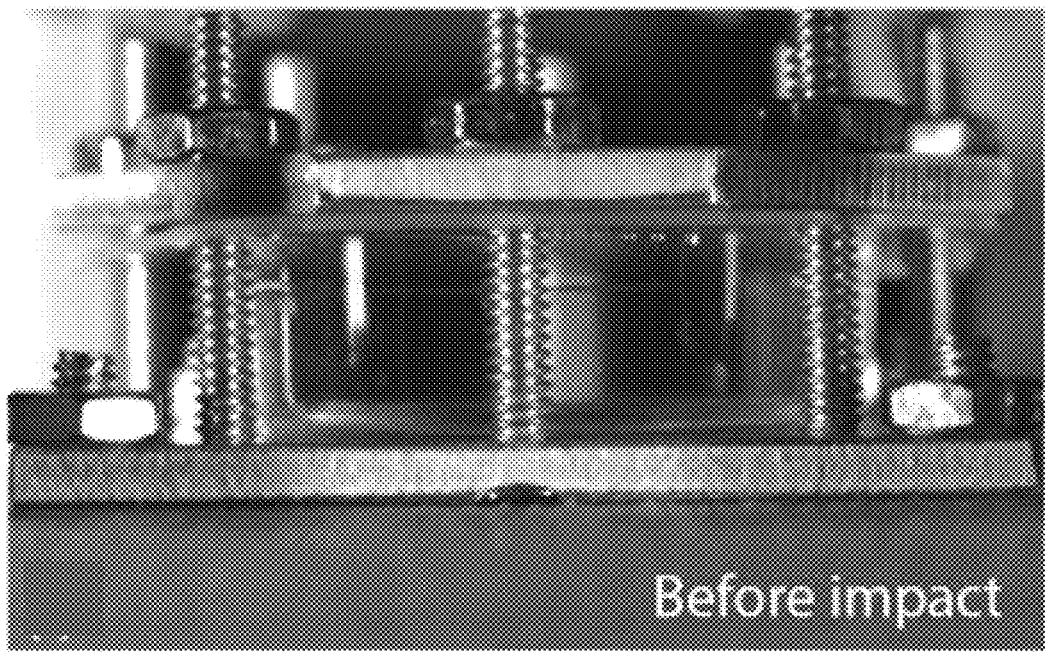
Figure 3J:
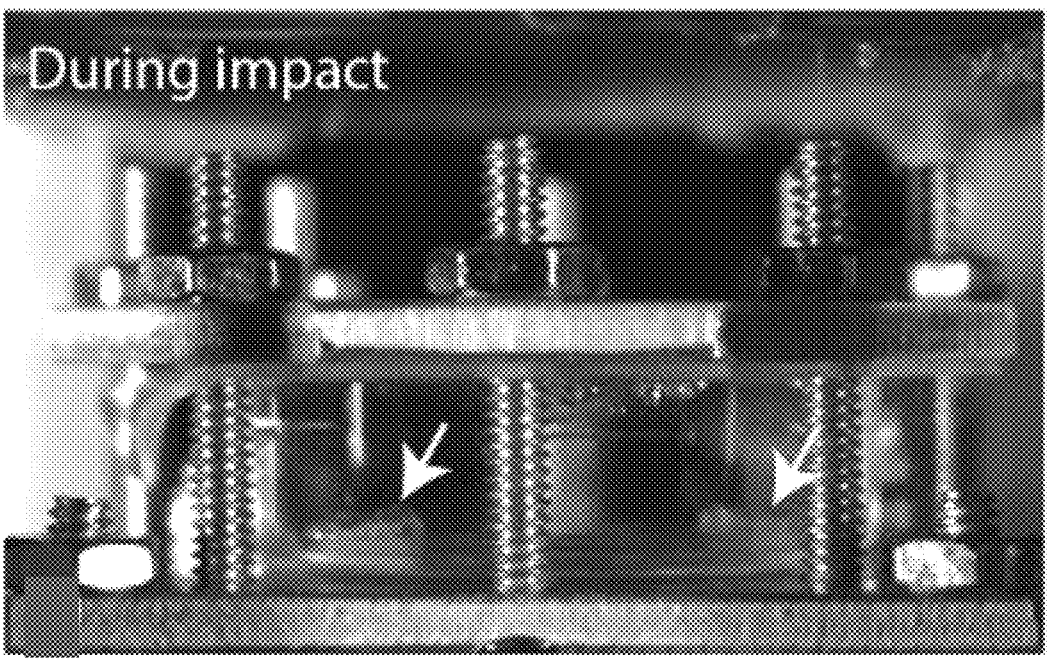

FIGS. 3A-3J show the characterization of the critical mechanical impact for cell injury using Hs27 cells. The average confluency curves provide data for 160 hours of monitoring for a 5 cm single drop, a 10 cm single drop and a 20 cm single drop (FIG. 3A); a 15 cm single drop, a 20 cm single drop, a 10 cm five time drop, a 15 cm five time drop, and a 20 cm five time drop (FIG. 3B); and a 30 cm single drop and a 40 cm single drop on the cell cultures. Passage 6, 8, and 11 were used for the data in FIGS. 3A, 3B, and 3C, respectively. The acceleration measured during the 30 cm and 40 cm drops are shown in the inset of FIG. 3C. The local confluency curves for Control 2, the 30 cm drop, and the 40 cm drop from FIG. 3C are shown in FIGS. 3D, 3E, and 3F, respectively. FIGS. 3G and 3H show live cell images corresponding to C3 in FIG. 3F before (FIG. 3G) and after (FIG. 3H) the impact. FIGS. 3I and 3J show high speed camera images of the cell culture setup during the 40 cm drop. FIG. 3I shows an image before impact. FIG. 3J is an image during impact showing cativation bubbles on the petri dish (indicated by arrows).

The cell cultures that were exposed to less than 40 cm drop, both single and multiple impact conditions, show the average as well as local confluency curves that are very similar to the corresponding Control 2 results. On the contrary, the average confluency after the 40 cm-drop experiment decreased from 48% to 35%. Furthermore, the local confluency curves indicated that the cell damage was not homogeneous over the entire petri dish as significant loss of cell population was localized to C3, D2, and E3 in FIG. 3F. As an example, the local confluency in C3 significantly dropped from ~40% to ~3%. This dramatic change is also shown in FIG. 3G and FIG. 3H, live cell images before and after a 40 cm-drop, respectively.

Based on the experimental data summarized in FIGS. 3A-3J, the critical drop height associated with the noticeable loss of cell population was >30 cm. The amplitude of input acceleration for 30 cm-drop is 990-1000 G (see the inset in FIG. 3C). Since, the maximum acceleration-induced pressure is linearly proportional to the size of biological system, the critical input acceleration associated with cell damage would significantly increase with decreasing size of biological systems.

Another observation is a sudden increase in localized cell death for 40 cm-drops, rather than globally and incrementally increasing cell death, where the corresponding amplitude of acceleration is 1280-1370 G (see the inset in FIG. 3C). To identify the specific damage mechanism that seems to be activated for >1000 G, high-speed camera movies were utilized. FIGS. 3I and 3J are the high speed images showing that cavitation bubbles form at the bottom of a petri dish for 40 cm-drops, which are likely responsible for localized cell damages considering the violent nature of cavitation dynamics.

To access the plasma membrane integrity of individual cell populations after a 40 cm-drop, propidium iodide (PI) were implemented. Cells stained with this dye indicate a compromised plasma membrane because PI is impermeable to healthy cells. There were at least three areas on a petri dish that were subject to cavitation. Among the remaining cells, approximately 10% of fibroblasts were stained PI 3 hours after impact. 48 hours afterward the impact, the cell population had doubled and no cells were observed stained with PI. To assess the fate of cells showing positive PI staining, the relative PI levels in individual cells over time were analyzed. The morphology and positions of the cells changed over the course of 24 hours, indicating that the fibroblasts are motile. One cell exhibited a significantly reduced fluorescence intensity after 3 hours, whereas the 2nd cell exhibited a more gradual reduction in fluorescence intensity over the course of 25 hours. At 24 hours, a new cell stained with a large fluorescence intensity entered the region, suggesting that the reduction in cell PI staining is not due to photobleaching. 48 hours after impact, no PI staining was observed in the cell population, indicating that fibroblasts plasma membrane was repaired over time.

Thus, acceleration alone does not damage fibroblasts even when applied acceleration (~1000 G) was significantly greater than the conventional injury criterion, 150 G. On the contrary, mechanical impact corresponding to the onset of cavitation bubbles resulted in sudden cell damage. Because dynamics of cavitation bubbles is stochastic and localized, significant loss of cell population is limited to randomly distributed, localized spots on a 2D cell culture plate in the cell culture chamber. Among the remaining cells in the damaged spots, cell membrane damage was detected utilizing fluorescent imaging techniques.

Cavitation

Acceleration-induced pressure did not result in cell detachment or change in cell growth curves when $a_{in} < a_{cr}$ where $a_{in}$ is the amplitude of input acceleration and $a_{cr}$ is the critical acceleration for cavitation. In this case, the acceleration-induced pressure at the bottom of a petri dish (where cells are) during the impact event ($0<t<1$ ms) is expected to be tensile. In addition, the amplitude of tensile pressure would be less than the critical pressure for cavitation nucleation in pure liquid, 110 kPa. On the other hand, the cells that were directly under the influence of cavitation bubbles were significantly damaged.

One possible explanation for this significant difference in cell response before and after impact is that the amplitude of cavitation-induced pressure may be much larger than acceleration-induced pressure. However, a recent study reported that pressure associated with bubble collapse of thermally induced cavitation is about 56 kPa (Chen et al., Astrocyte Viability and Functionality in Spatially Confined Microcavitation Zone, ACS Appl Mater Interfaces (2019)), which is considerably smaller than the critical pressure, using a pressure sensitive film. Another possible mechanism is that cavitation-induced pressure, i.e., a rate of the pressure change in time, is much faster than acceleration-induced pressure and, as a result, viscoelastic response of cells, i.e., cell damage response, at different loading could be significantly different.

To quantitatively consider the two possible damage mechanisms above, transparent plastic tubes were prepared with an inserted pressure sensor for measuring time-varying pressure at the bottom of the tube. A transparent plastic tube was filled with 6 ml pure water, and a pressure sensor was inserted at the bottom. This experiment setup allowed concurrent measurements of acceleration and pressure at the liquid-plate interface, which mimics the cell culture media and plate interface at the bottom of the cell culture chamber.

Measurements were made for acceleration and acceleration-induced pressure for 30 mm and 40 mm drop experiments utilizing a plastic tube filled with 6 ml pure water (H~40 mm). For $h_{drop}$=30 mm, the smooth profile of the acceleration signal and measured pressure were very similar with a small shift in phase likely due to viscosity of water. The measured amplitudes of acceleration and pressure were $a_{min}$=-140.2 G and $p_{min}$=-96.9 kPa, respectively. In addition, shock waves, i.e., pulse-like signals, were not observed in the pressure measurement.

For $h_{drop}$=40 mm, qualitative trends within $t<1$ ms were very similar to $h_{drop}$=30 mm. As expected, the amplitudes of acceleration and pressure increased to $a_{min}$=-174.7 G and $p_{min}$=-118.6 kPa, respectively, due to the increasing drop height. Although the qualitative acceleration profiles of the both drops do not change much, the corresponding pressure measurement for $h_{drop}$=40 mm became significantly different for $t>1$ ms, i.e., rapid tensile/compressive pressure cycles superposed with much higher frequency acceleration signals.

To reveal a main mechanism that corresponds to the sudden changes in pressure, we performed image analysis of high-speed camera movies that are synchronized with acceleration and pressure measurements in time. A likely cavitation nucleation site had a maximum local pressure at different time points. The cavitation nucleation was first detected around t=0.64 ms. The bubbles grew in size until t=0.84 ms and then fully collapsed after t=1.00 ms. These images strongly indicated that the sudden changes in the pressure were mainly associated with dynamics of cavitation bubbles, in particular, cavitation collapse.

The amplitude of cavitation-induced pressure is considerably larger than acceleration-induced pressure and a rate of pressure changes for cavitation-induced pressure is significantly faster than acceleration-induced pressure. Upon impact, the amplitude of acceleration-induced pressure gradually increased from 0 at t=0 ms to 118.6 kPa at t=0.70 ms. On the other hand, cavitation-induced pressure increased from -72.9 to 259.2 kPa within 0.05 ms where the maximum pressure occurred at t=1.11 ms. Note that the corresponding rates of pressure change for acceleration- and cavitation-induced pressure are 169 kPa/ms and 6642 kPa/ms, respectively.

The acceleration-induced pressure (t<1 ms) for both $h_{drop}$=30 and =40 mm strongly suggests that the 1 mm-thick foam at the top of the sample holder effectively eliminates possible propagation of shock waves to the liquid and pressure in the liquid is indeed acceleration-induced. One possible implication of the results is that the effect of shock waves on mild blunt injury is unlikely significant because the human body is protected by soft skin, which would behave as the 1 mm-thick from layer.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A method for in vitro characterization of cell injury due to mechanical blunt, the method comprising:
   imaging in vitro live cell populations in a cell culture setup in an incubator using a live cell imaging instrument;
   removing the cell culture setup from the incubator and placing the cell culture setup in a holder for an impact system, wherein there is a first foam above the holder and a second foam below the holder;
   applying at least one controlled impact to the cell culture setup;
   quantifying velocity, acceleration, impact force, and cavitation induced pressure during impact while optically monitoring the cell culture setup;
   after impact, imaging the in vitro live cell populations in the cell culture setup in an incubator using the live cell imaging instrument;
   analyzing the in vitro live cell populations using optical, biological, and mechanical measurements;
   monitoring the dynamic response of the in vitro live cells populations for up to two weeks; and
   mapping out the relationship between cell injury and mechanical blunt over time.

2. The method of claim 1, wherein multiple in vitro live cell populations can be imaged simultaneously in a multiplex arrangement.

3. The method of claim 1, wherein the first foam is 1 mm thick and 4 MPa and the second foam is 12 mm and 0.4 MPa.

4. A system for in vitro characterization of cell injury due to mechanical blunt, the system comprising:
   an impact system comprising a holder, a first foam above the holder, and a second foam below the holder;
   at least one camera;
   an incubator;
   a live cell imaging instrument;
   a cell culture setup comprising an in vitro live cell population, wherein the cell culture setup is placed in an incubator for live cell imaging before and after impact, and wherein the cell culture setup is placed in the holder for impact; and
   a data acquisition system.

5. The system of claim 4, wherein the cell culture setup comprises multiple cell populations that can be imaged simultaneously in a multiplex arrangement.

6. The system of claim 4, wherein the first foam is 1 mm thick and 4 MPa and the second foam is 12 mm and 0.4 MPa.

* * * * *